United States Patent
Giroux et al.

(10) Patent No.: US 6,575,917 B2
(45) Date of Patent: Jun. 10, 2003

(54) PROTECTIVE-SLEEVE CARTRIDGE AND STETHOSCOPE INCORPORATING SAME

(75) Inventors: Jennifer S. Giroux, Cincinnati, OH (US); Jack E. Smith, Dayton, OH (US); John R. Cremons, Cincinnati, OH (US); William S. Smith, Jr., Cincinnati, OH (US)

(73) Assignee: St. Joseph Solutions LLC, Springboro, OH (US)

( * ) Notice: Subject to any disclaimer, the term of this patent is extended or adjusted under 35 U.S.C. 154(b) by 0 days.

(21) Appl. No.: 10/095,784

(22) Filed: Mar. 12, 2002

(65) Prior Publication Data

US 2002/0138015 A1 Sep. 26, 2002

Related U.S. Application Data

(60) Provisional application No. 60/275,724, filed on Mar. 14, 2001.

(51) Int. Cl.[7] .................................................. A61B 7/02
(52) U.S. Cl. ........................................ 600/528; 181/131
(58) Field of Search .............................. 181/130, 131; 600/528; D24/134; 381/67

(56) References Cited

U.S. PATENT DOCUMENTS

| | | | |
|---|---|---|---|
| 1,331,112 A | 2/1920 | Lazar | 221/51 |
| 3,213,960 A | 10/1965 | Wagner | 181/126 |
| 3,861,395 A | 1/1975 | Taniguchi | 604/172 |
| 3,999,625 A | * 12/1976 | Pickett et al. | 181/131 |
| 4,461,368 A | 7/1984 | Plourde | 181/131 |
| 4,598,417 A | * 7/1986 | Deno | 381/67 |
| 4,712,684 A | 12/1987 | Boeckmann | 206/554 |
| 4,757,381 A | 7/1988 | Cooper et al. | 348/66 |
| 4,867,268 A | * 9/1989 | Ulert | 181/137 |
| 4,871,046 A | 10/1989 | Turner | 181/131 |
| 5,466,897 A | 11/1995 | Ross et al. | 181/131 |
| 5,466,898 A | 11/1995 | Gilbert et al. | 181/131 |
| 5,486,659 A | 1/1996 | Rosenbush | 181/131 |
| 5,539,162 A | 7/1996 | Tuttle | 181/131 |
| 5,564,431 A | * 10/1996 | Seward | 128/715 |
| D376,043 S | 12/1996 | Rix | D3/203 |

(List continued on next page.)

OTHER PUBLICATIONS

L. Martelli, *International Search Report*, Jul. 25, 2002, International Application No. PCT/US02/07549.
US patent application Pub. No.: US 2001/0001188 A1, published May, 2001.
US patent application Pub. No.: US 2001/0045319 A1, published Nov. 2001.

*Primary Examiner*—Carl Layno
(74) *Attorney, Agent, or Firm*—Wood, Herron & Evans, LLP

(57) ABSTRACT

A protective-sleeve-cartridge/stethoscope assembly includes a stethoscope and a cartridge mounted to the stethoscope, with the cartridge including a sleeve. In a cartridge-and-sleeve assembly, the assembly includes a cartridge having a first elongated circumferential sidewall, with the first elongated circumferential sidewall defining an interior space. The assembly further includes a sleeve, at least a part of which is stored in the interior space. In this assembly, the cartridge and sleeve are constructed and arranged whereby the cartridge may be mounted to a stethoscope, and at least a part of the sleeve may be dispensed from the cartridge interior space and over a head of the stethoscope. A cartridge for mounting to a stethoscope includes a first elongated circumferential sidewall and a second elongated circumferential sidewall inwardly spaced from the first sidewall. The first and second sidewalls define, between them, a first interior space, with the first interior space constructed and arranged to contain at least a part of a sleeve. The cartridge further includes a first end, and a selectively-moveable cover at the first end, with the cover being moveable between an open position and a closed position, whereby a user may adjust access to the first interior space.

32 Claims, 5 Drawing Sheets

U.S. PATENT DOCUMENTS

| | | |
|---|---|---|
| 5,592,946 A | 1/1997 | Eddy .......................... 600/528 |
| 5,623,131 A | 4/1997 | Earnest ...................... 181/131 |
| 5,747,751 A | 5/1998 | Weckerle et al. ........... 181/131 |
| 5,808,244 A | 9/1998 | Knight et al. ............. 181/131 |
| 5,819,739 A | 10/1998 | Levavi et al. ............... 600/499 |
| 5,921,941 A | 7/1999 | Longobardo et al. ....... 600/528 |
| 5,949,032 A | 9/1999 | Wurzburger ................ 181/131 |
| 6,006,856 A | 12/1999 | Skubal et al. ............... 181/131 |
| 6,019,187 A | 2/2000 | Appavu ...................... 181/131 |
| 6,041,889 A | 3/2000 | Stark et al. ................. 181/131 |
| 6,165,035 A | 12/2000 | Avner .......................... 446/72 |
| 6,186,957 B1 | 2/2001 | Milam ........................ 600/528 |
| 6,206,134 B1 | 3/2001 | Stark et al. ................. 181/131 |
| 6,279,677 B1 | 8/2001 | Sanchez-Zambrano ...... 181/131 |

\* cited by examiner

PROTECTIVE-SLEEVE CARTRIDGE AND STETHOSCOPE INCORPORATING SAME

CROSS-REFERENCE TO RELATED APPLICATION

This application claims the benefit of the filing date of Provisional U.S. Patent Application No. 60/275,724, entitled "Disposable Cover System and Stethoscope Incorporating Same" and filed on Mar. 14, 2001. The entire disclosure of U.S. Provisional Patent Application No. 60/275,724 is hereby incorporated into this non-provisional U.S. patent application by reference.

BACKGROUND OF THE INVENTION

1. Field of the Invention

This invention is directed to stethoscope covers, and more particularly, to stethoscope covers which cover the head of a stethoscope.

2. Description of the Related Art

The stethoscope is a clinical, diagnostic instrument used to conduct, or transmit, sounds produced in a patient's body to one or both ears of a clinician. Because of the diagnostic importance of the stethoscope, virtually every clinician has a stethoscope, and uses that same stethoscope throughout the day. For example, a clinician may use their stethoscope during examination of patients in a physician's office, in a hospital clinic, in an emergency room, and while examining hospital in-patients. By using their stethoscope, the clinician is able to transmit respiratory, cardiac, plural, arterial, and other sounds to the ear(s) of the clinician, by applying the head of the stethoscope to the patient's chest, back, abdomen, arms, and other areas. Depending upon the particular patient, any one or more of these areas may be secreting bodily fluids contaminated with infectious agents, including, for example, viruses such as the human immunodeficiency virus ("HIV"), resulting in the contamination of the stethoscope head. And, unless the clinician sterilizes their stethoscope between each patient examination, each subsequent patient's skin would be contaminated with any infectious agents which may have been present on at least the prior patient, and more likely, an accumulation of infectious agents of all of the clinician's preceding patients for the day.

In practice, however, the vast majority of medical personnel do not clean or sanitize their respective stethoscopes between examinations of different patients. Accordingly, while helpful and seemingly innocuous, in truth, stethoscopes end up transmitting any of a number of different infectious agents from one patient to another. And, as noted briefly above, depending upon the nature of the infectious agent, as well as the health-status of the various patients, an otherwise healthy patient may become sick, and in some cases a patient may even die as a result of the infectious agent or agents transferred via the contaminated head of the stethoscope.

SUMMARY OF THE INVENTION

The invention overcomes the drawbacks and limitations described above by providing a protective-sleeve cartridge which is mountable directly onto a stethoscope. In this fashion, a clinician does not have to return to a particular counter top or other location where a box of covers is stored, remove a single cover from the dispenser, and pull the cover up and over the head of the stethoscope—all of this needing to be done before seeing the next patient. Instead, because the protective sleeve cartridge is located on the stethoscope itself, it stays with the clinician at all times, thereby making it quick and easy for the clinician to have an unused protective sleeve portion covering the stethoscope head, each and every time the clinician examines a different patient.

In further detail, one aspect of the invention is directed to a combination of a stethoscope and a cartridge mounted to the stethoscope, with the cartridge including a sleeve. The cartridge is shaped and fabricated so that it easily may be mounted to a stethoscope, so that the combination of stethoscope and cartridge are comfortable for the clinician to wear and use, and so that the clinician easily may selectively and progressively lower an unused portion of the sleeve from the cartridge to the stethoscope head. The sleeve, itself, includes a plurality of longitudinally-spaced sleeve portions; and, if desired, the sleeve portions may be separated by perforations. Each sleeve portion has a leading end and a fastener at the leading end, whereby a clinician easily and quickly may adjust the leading end from an open position to a closed position, thereby further protecting the stethoscope head, and thus each patient, from cross-contamination. One such fastener is an adhesive.

Initially, the vast majority, if not all, of the sleeve is accordion-folded in the cartridge. In this fashion, a clinician simply pulls downward or outward on the outermost sleeve portion until an unused sleeve portion covers the stethoscope head, a movement which progressively moves an additional section of the accordion-folded sleeve from the cartridge.

If desired, the cartridge may include a first elongated circumferential sidewall, with the first elongated circumferential sidewall defining an interior space. Also, if desired, the first elongated circumferential sidewall may be a tube or may include a tube. In one version, the first elongated circumferential sidewall has a cross-sectional shape which is substantially oval. Also, when the cartridge includes a first elongated circumferential sidewall, at least a part of the sleeve may be positioned within the interior space of that circumferential sidewall. If desired, the cartridge may have a selectively-moveable cover at its first end, with the cover being moveable between an open position and a closed position. In this fashion, a clinician easily may adjust access to the interior space of the first elongated circumferential sidewall.

In addition, if desired, the cartridge may include a second elongated circumferential sidewall, inwardly spaced from the first elongated circumferential sidewall, with these first and second sidewalls defining between them a first interior space. When the second elongated circumferential sidewall is present, the sleeve, or a part of the sleeve, may be positioned within the first interior space. If desired, the second elongated circumferential sidewall may be releasably connected, either directly or indirectly, to the first elongated circumferential sidewall. Moreover, the first and second elongated circumferential sidewalls may be formed so that the connection is not only releasable, but also re-formable when the first and second circumferential sidewalls are disconnected.

If desired, the cartridge may have a fastener at its second end, with the fastener shaped and designed to fasten the cartridge to a stethoscope. The fastener may be, or may include, a cap, with the cap being releasably connected to the first- and/or second-elongated circumferential sidewall(s). The cap may include an opening and a circumferential surface defining the opening, with the circumferential surface being sized, shaped, and positioned to secure the cap to a stethoscope.

Another aspect of the invention is directed to a combination of a cartridge and a sleeve, with the cartridge for mounting to a stethoscope, and the sleeve for covering the head of the stethoscope. The combination includes: a cartridge having a first elongated circumferential sidewall, with the sidewall defining an interior space; and a sleeve, with at least a part of the sleeve being stored in the interior space. The cartridge and sleeve are constructed and arranged so that the cartridge may be mounted to a stethoscope, and at least a part of the sleeve may be dispensed from the cartridge interior space and over a head of the stethoscope.

A further aspect of the invention is directed to a cartridge for mounting to a stethoscope, and for dispensing a sleeve over a sensing head of the stethoscope. The cartridge includes: a first elongated circumferential sidewall; a second elongated circumferential sidewall inwardly spaced from the first sidewall, with the first and second sidewalls defining between them a first interior space, the first interior space constructed and arranged to contain at least a part of a sleeve; a first end; and a selectively-moveable cover at the first end, with the cover being moveable between an open position and a closed position, thereby allowing a clinician to adjust the access to the first interior space.

BRIEF DESCRIPTION OF THE DRAWINGS

The accompanying drawings, which are incorporated in, and constitute a part of, this specification, illustrate embodiments of the invention and, together with the general description of the invention given above, and the detailed description of versions of the invention given below, serve to explain the principles of the invention.

DETAILED DESCRIPTION OF THE DRAWINGS

Figure 1:
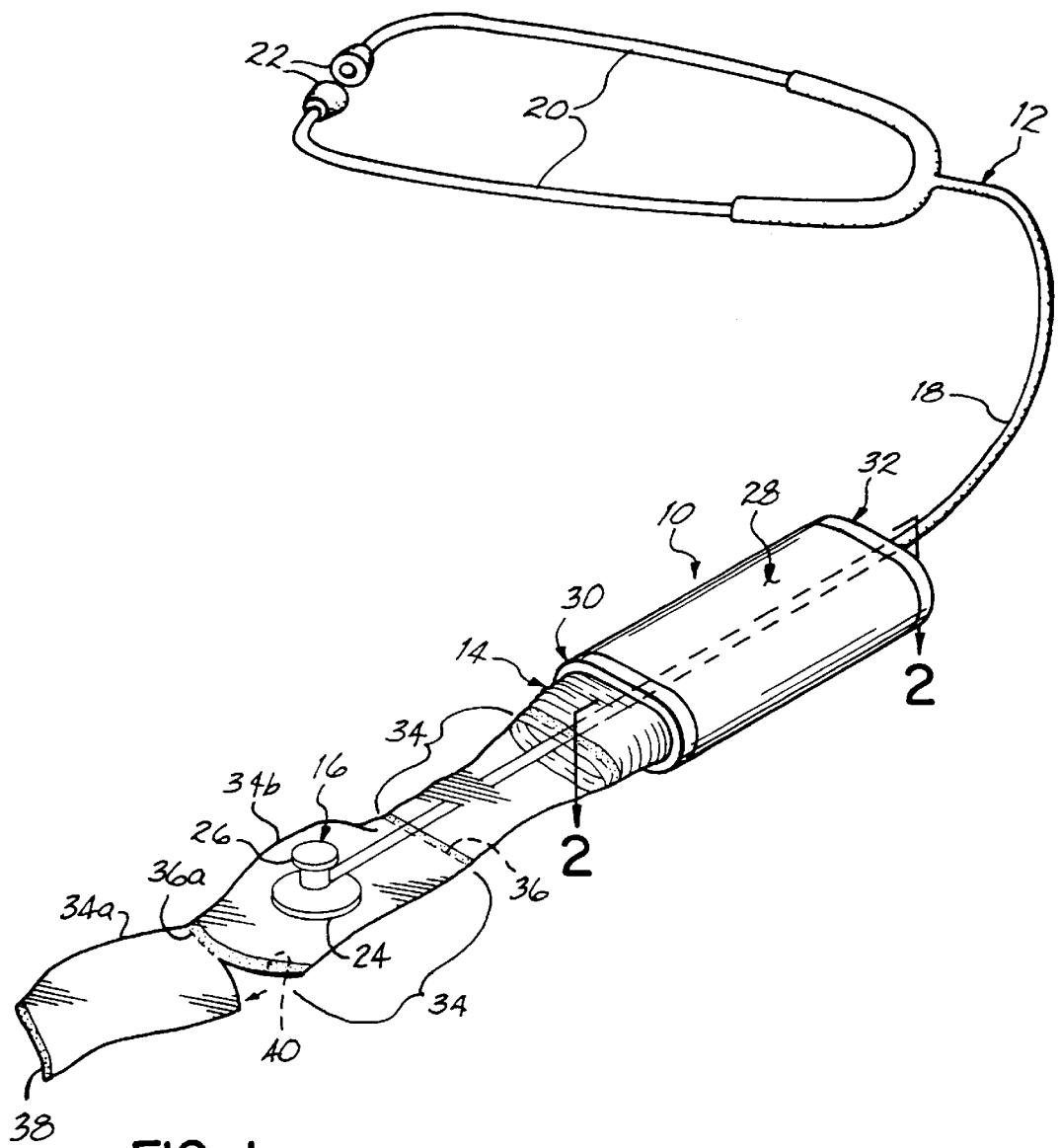
FIG. 1 is perspective view of one version of the invention.

The version of the invention shown in FIG. 1 includes a cartridge 10 mounted to a stethoscope 12, with the cartridge including a sleeve 14.

The stethoscope 12 shown is a binaural stethoscope with a head 16, a sound tube 18 connected to the head 16, and a pair of earpiece tubes 20 connected to the sound tube 18, with each earpiece tube having an ear tip 22. The head 16, itself, includes both a diaphragm 24 and a bell 26. In this fashion, a sound may be transmitted into the head 16 of the stethoscope 12 via the diaphragm 24, and conducted up the sound tube 18 into each of the earpiece tubes 20, thereby enabling a clinician to listen to any of a number of different body sounds.

The sleeve-containing cartridge 10 is mounted directly to the sound tube 18, thereby providing an all-in-one protective-sleeve/stethoscope combination. This feature, alone, is of tremendous benefit to the clinician because the sleeve-containing cartridge 10 is always with the clinician's stethoscope. In further detail, the cartridge 10 includes a first elongated circumferential sidewall 28 which defines an interior space, with the protective sleeve 14 being accordion-folded in this interior space (not shown). The cartridge 10 also includes a selectively-moveable cover 30 at its first end, and a fastener in the form of a cap 32 at its second end. The sleeve 14, itself, is made up of a series of longitudinally-spaced sleeve portions 34, with the sleeve portions 34 being separated by perforations 36. Each sleeve portion 34 has a leading end 38 and, as shown, a fastener in the form of an adhesive 40 on the interior surface of the leading end 38. Although the leading-end fastener is shown in the form of an adhesive 40, the fastener may be any suitable element or combination of elements, as will be appreciated by those of ordinary skill in the art.

As shown in FIG. 1, the outermost sleeve portion 34a is a used sleeve portion. Accordingly, a clinician (not shown) has pulled outward or downward on this outermost sleeve portion 34a, thereby bringing the adjacent, unused sleeve portion 34b into position about the stethoscope head 16. The clinician also has sealed the leading end 38 of the unused sleeve portion 34b, and has started to remove the used sleeve portion 34a by tearing it off of the sleeve 14 at the perforation line 36a.

Figure 2:
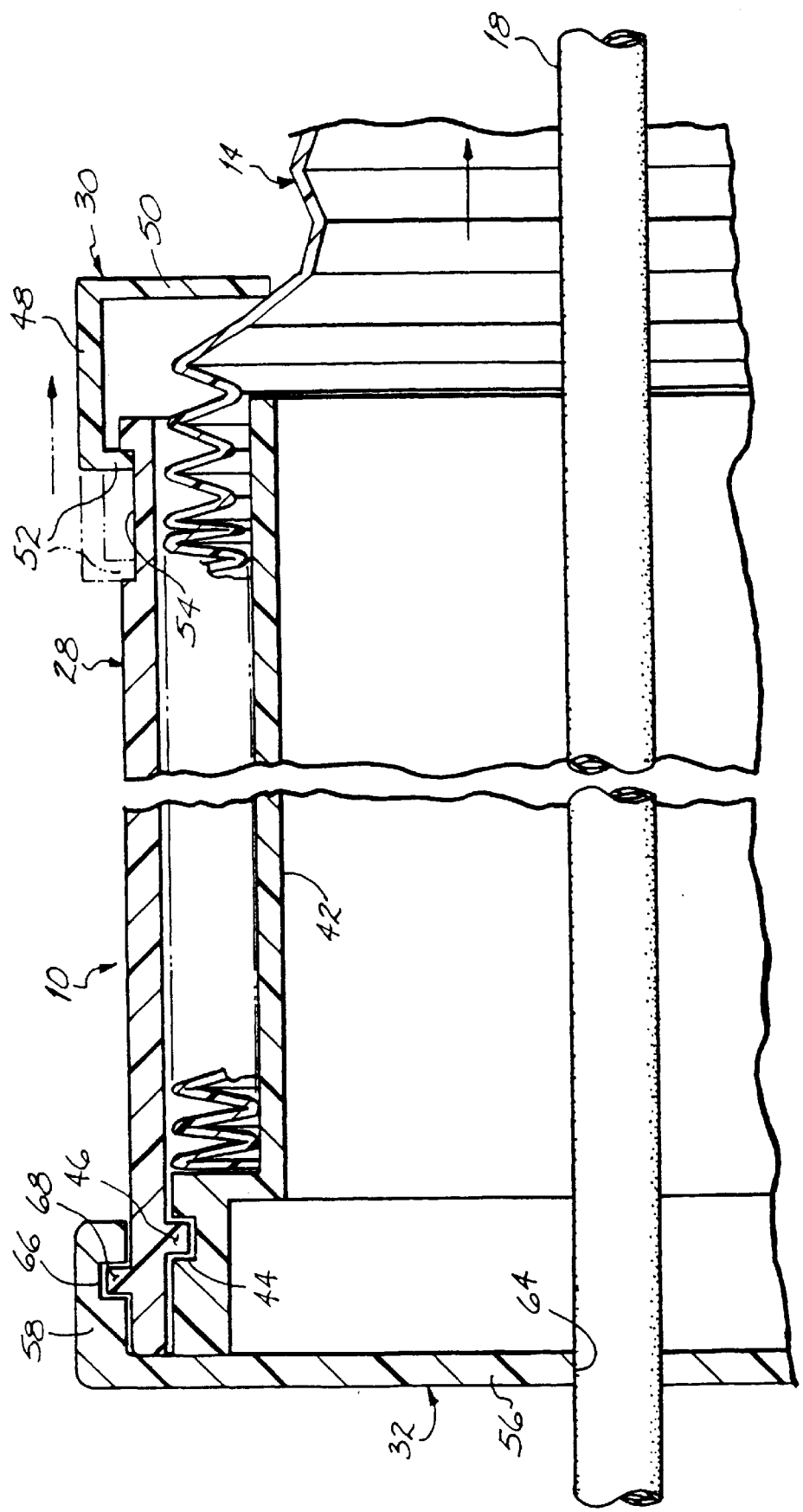
FIG. 2 is a partial cross-sectional view of a portion of the version of FIG. 1.

FIG. 2 shows the cartridge 10 of FIG. 1 in greater detail. More specifically, the cartridge 10 includes not only the first elongated circumferential sidewall 28, but also, a second elongated circumferential sidewall 42 inwardly spaced from the first sidewall 28. These first and second sidewalls 28,42 define between them a first interior space which contains the sleeve 14, folded in an accordion-like fashion. For the particular cartridge 10 shown, the second elongated circumferential sidewall 42 is a component which is separate from the first elongated circumferential sidewall 28. This feature is beneficial because it creates several different options for how the cartridge 10 may be made and used. For example, if desired, the second elongated circumferential sidewall may be a disposable unit which may be pre-loaded with an accordion-folded sleeve about its exterior surface. In this fashion, after a clinician uses the last sleeve portion of a given sleeve, the clinician may simply dispose of the second elongated circumferential sidewall, and releasably attach a new second elongated circumferential sidewall within the interior space of the cartridge, with the new sidewall having been pre-loaded with a full accordion-folded sleeve. As shown in FIG. 2, the second elongated circumferential sidewall 42 has a circumferential groove 44 adjacent its upper end, with the groove 44 releasably engaging a corresponding bead 46 which extends from the inner surface of the first elongated circumferential sidewall 28 at its second end, in a circumferential fashion. This system allows the clinician to disconnect, and if desired, to reconnect, a given second elongated circumferential sidewall 42 to the first elongated circumferential sidewall 28. In addition, as described briefly above, it allows for easy replacement of a spent inner cartridge (i.e., second elongated circumferential sidewall) with a fresh inner cartridge, that is, a cartridge having a full-length sleeve of protective sleeve portions.

FIG. 2 also shows the selectively-moveable cover 30 in greater detail. This cover has a circumferential sidewall 48, a bottom wall 50 connected to the bottom end of the sidewall 48, and an inwardly-extending circumferential bead 52 at the top end of the sidewall 48. The bottom wall 50 has an opening which is sized so as to enable the head (not shown) of a stethoscope to pass through the opening. In addition, the bottom wall 50 has a width which is somewhat greater than the width of the first interior space defined by the first and second elongated circumferential sidewalls 28,42. As may be seen, the bead 52 of the selectively-moveable cover 30 rests in an elongated circumferential groove 54 at the first end of the first elongated circumferential sidewall 28. In this fashion, a clinician may move the selectively-moveable cover 30 between a fully-open position and a fully-closed position (shown in phantom). When the moveable cover 30 is in a partially- or fully-open position, a clinician may draw out an additional section of the sleeve 14 from the cartridge 10, with ease. And when the moveable cover 30 is in the fully-closed position (shown in phantom), the bottom wall 50 of the cover 30 closes the otherwise open end of the first interior space. In this fully-closed position, the moveable cover 30 assists in keeping the accordion-folded sleeve 14 in its current position. Also, in this fully-closed position, the moveable cover 30 serves to protect the section of sleeve 14 contained in the first interior space.

Figure 3:
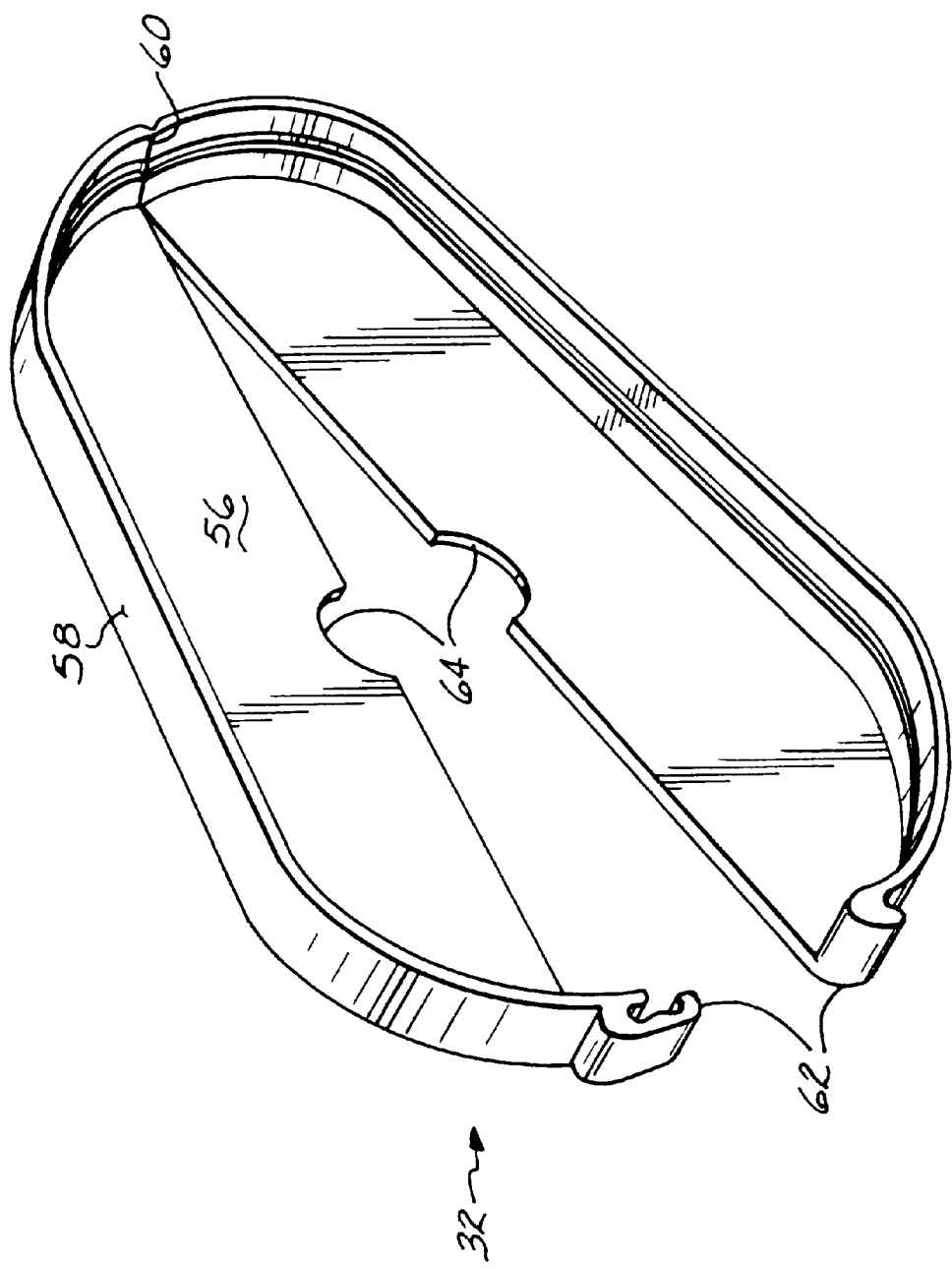
FIG. 3 is a perspective view of a component of the version of FIG. 1.

As best seen in FIGS. 2 and 3, this version of the cartridge 10 includes an upper fastener in the form of a split cap 32. As shown in FIG. 3, the cap 32 includes a top wall 56 and a circumferential sidewall 58 which depends from the top wall 56. The cap 32 has two halves connected by a living hinge 60 at one end of the cap 32, and by a latch 62 at the other end. The top wall 56 includes a circular opening defined by a circumferential surface 64 which releasably clamps onto the sound tube 18 of the stethoscope 12. The circumferential sidewall 58 of the cap 32 includes a groove 66 which extends circumferentially along the interior surface of the sidewall 58. As best seen in FIG. 2, this groove 66 releasably engages a circumferential bead 68 which extends outward from the exterior surface at the second end of the first elongated circumferential sidewall 28. In this fashion, a clinician may position the cartridge 10 in any of a number of different positions along the length of the sound tube 18 simply by opening the latch 62 on the split cap 32, repositioning the cartridge 10, and re-fastening the latch 62. Accordingly, the clinician is able to custom-tailor the stethoscope-cartridge assembly to suit their individual preference. The cartridge 10, or any of its components, may be reusable or disposable, as desired. Typically, however, at least the sleeve 14 is disposable.

The various components of the cartridge may be made using any suitable disposable and/or reusable materials, with non-limiting examples including plastic and/or paperboard. For example, the second elongated circumferential sidewall may be made of cardboard or the like, with the circumferential groove at the upper end of the sidewall being formed in a plastic ring which may be conveniently attached to the cardboard tubing. The sleeve which surrounds the second elongated circumferential sidewall may be made of any suitable material, as would be appreciated by those of ordinary skill in the art. Non-limiting examples of such materials include, for example, thin, flexible, polymeric materials, such as polyethylene, latex rubber, silicone, soft vinyl, urethane, and the like. In addition, as will readily be appreciated by those of ordinary skill, a suitable cartridge may be made having any of a number of different cross-sectional shapes, with one non-limiting example being a circle. If a circular cross-sectional shape is used, and if desired, threads may be used for releasably engaging the first-sidewall 28 second end with the second-sidewall 42 upper end.

Figure 4:
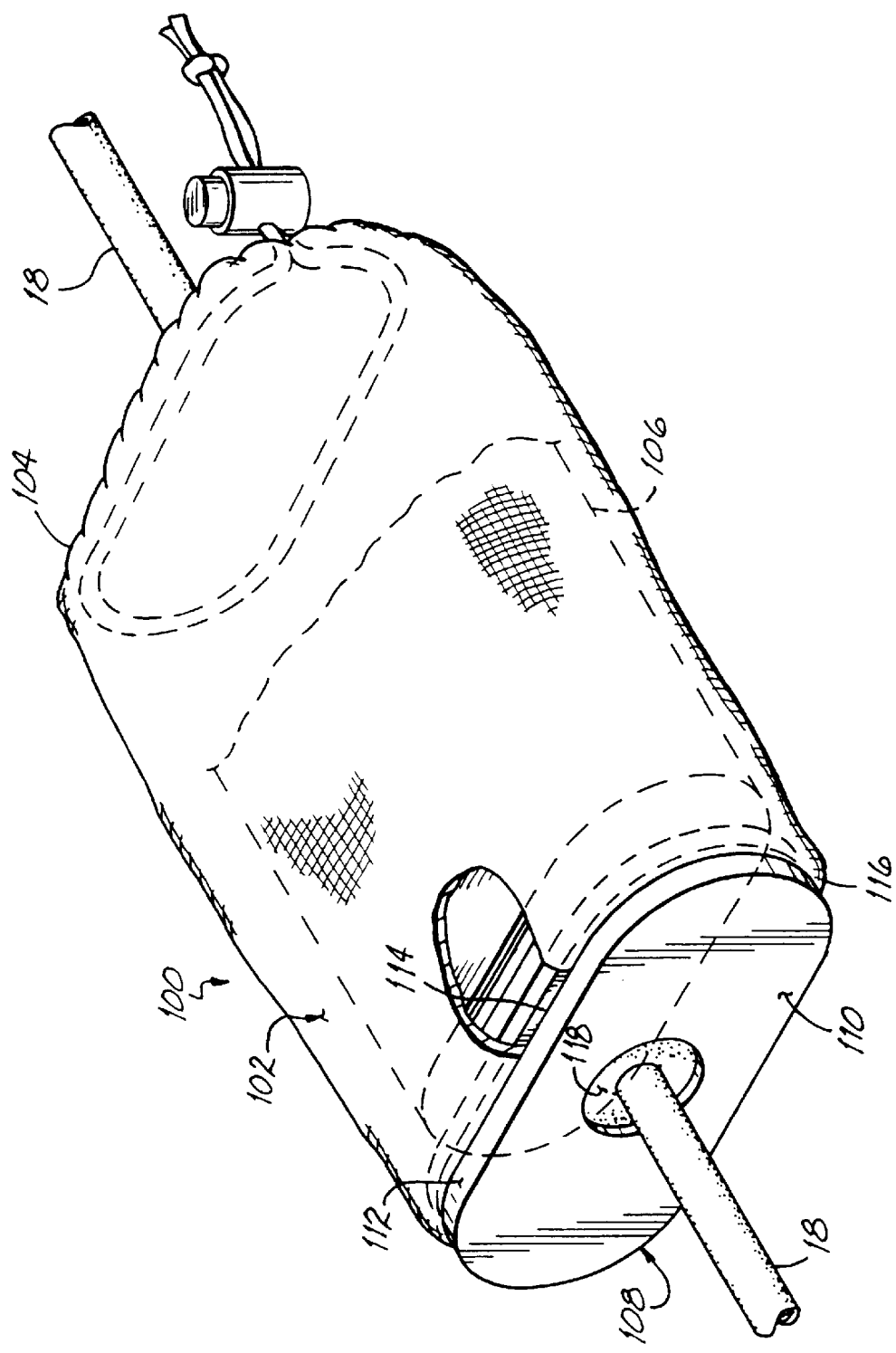
FIG. 4 is a perspective view, with a partial cutaway, of another version of the invention.

With reference to FIG. 4, another version of the cartridge 100 has a first elongated circumferential sidewall 102 which is made of any suitable commercially-available highly-flexible, drapable material, with one non-limiting example being nylon. In further detail, the first elongated circumferential sidewall 102 includes an elasticized closure 104 at its first end which is capable of completely covering the opening (not shown) of the first interior space defined by the first elongated circumferential sidewall 102 and the second elongated circumferential sidewall 106 (shown in phantom). For this cartridge 100, the upper fastener also is a cap 108 having a top wall 110 and a circumferential sidewall 112 depending from the top wall 110. In this version, however, the circumferential sidewall 112 has a groove 114 on its exterior surface which extends circumferentially. The first elongated circumferential sidewall 102 has an elastic cuff 116 at its second end which is releasably seated in the groove 114 of the cap 108. The top wall 110 of the cap 108 has two differently-sized, but concentric, openings. The smaller opening is slightly smaller than the cross-sectional diameter of the sound tube, and is defined by a resilient membrane 118, thereby enabling a clinician to position the cartridge 100 in any of a number of different positions along the sound tube 18 simply by sliding the cap 108 in one direction or the other along the length of the tube 18. The cartridge 100, or any of its components, may be reusable or disposable, as desired. Typically, however, at least the sleeve (not shown) is disposable.

Figure 5:
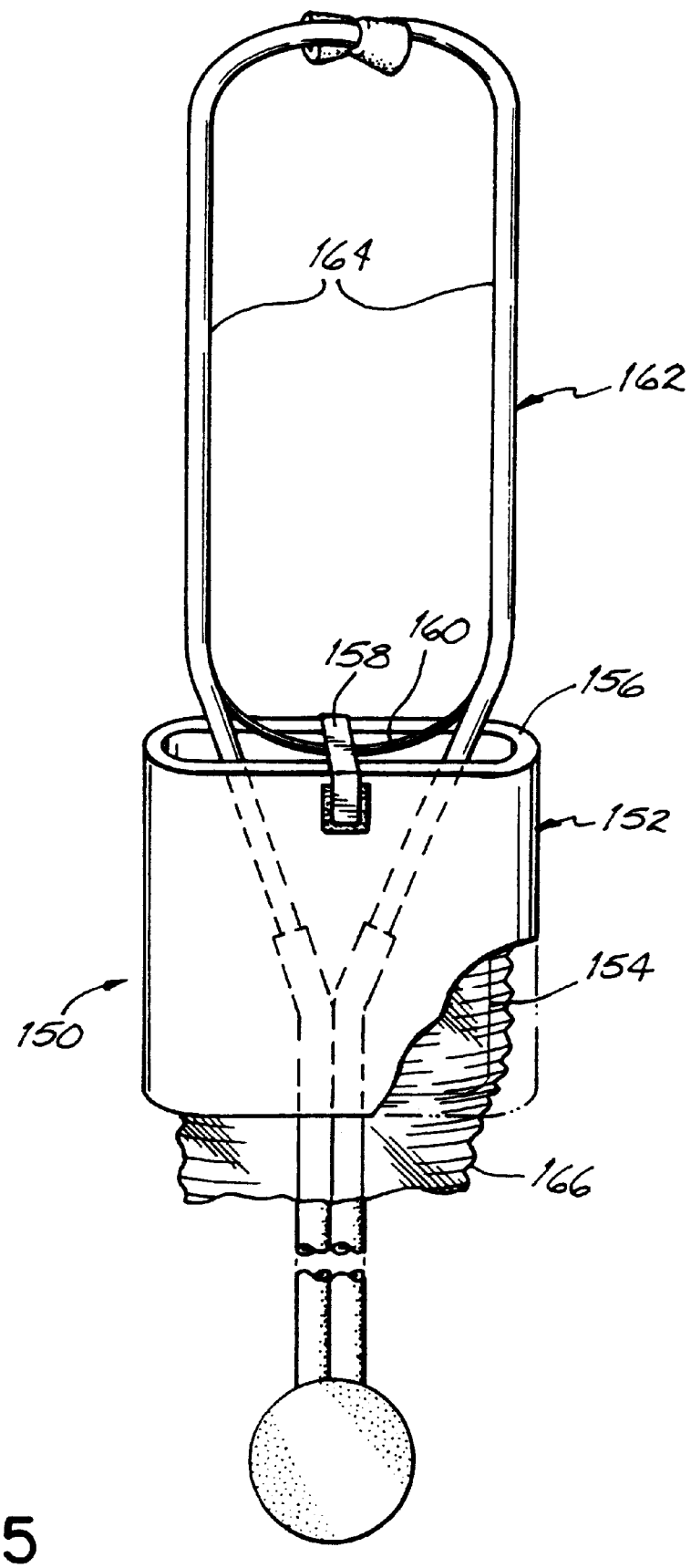
FIG. 5 is a perspective view, with a partial cutaway, of yet another version of the invention.

As shown in FIG. 5, in a further version, the cartridge 150 includes a first elongated circumferential sidewall 152 which is integrally connected to a second elongated circumferential sidewall 154 (shown in phantom) via a top wall 156. The cartridge 150 further includes an upper fastener in the form of a strap 158 which extends transversely across an upper opening of the cartridge 150, and which is releasably and resealably connected to the first elongated circumferential sidewall 152 at its second end, using hook- and loop-fasteners (not shown). However, the upper fastener may be made of any suitable material(s), as will be appreciated by those of ordinary skill. As shown in the Figure, the strap 158 is resting on a cross-bar 160 of the stethoscope 162, thereby supporting the cartridge 150 in position on the stethoscope 162. The cartridge 150, itself, has an oval cross-sectional shape, and is sufficiently wide so that a clinician may simply and easily slip the cartridge 150 over the binaural earpiece tubes 164 and cross-bar 160, and into position on the stethoscope 162. If desired, the cartridge 150 may further include a selectively-moveable cover (not shown) at the first end of the first elongated circumferential sidewall 152. The cartridge 150, or any of its components, may be reusable or disposable, as desired. Typically, however, at least the sleeve 166 is disposable.

While the present invention has been illustrated by a description of various versions, and while the illustrative versions have been described in considerable detail, it is not the intention of the inventor to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of the inventor's general inventive concept.

What is claimed is:

1. A combination, comprising:
   a stethoscope; and
   a cartridge mounted to the stethoscope, the cartridge including a sleeve,
   wherein the stethoscope has a head, the cartridge and the sleeve constructed and arranged whereby the sleeve may cover the head.

2. The combination of claim 1 wherein the sleeve includes a plurality of longitudinally-spaced sleeve portions.

3. The combination of claim 2 wherein the sleeve portions are separated by perforations.

4. The combination of claim 3 wherein each sleeve portion has a leading end and a fastener at the leading end, the fastener constructed and arranged whereby a user may alter the leading end from an open position to a closed position.

5. The combination of claim 1 wherein the sleeve is accordion-folded.

6. The combination of claim 1 wherein the cartridge includes a first elongated circumferential sidewall, the first elongated circumferential sidewall defining an interior space.

7. The combination of claim 6 wherein the first elongated circumferential sidewall includes a tube.

8. The combination of claim 6 wherein the first elongated circumferential sidewall has a cross-sectional shape which is substantially oval.

9. The combination of claim 6 wherein at least a part of the sleeve is disposed within the interior space.

10. The combination of claim 6 wherein the cartridge has a first end and a selectively-moveable cover at the first end, the selectively-moveable cover moveable between an open position and a closed position, whereby a user may adjust access to the interior space.

11. The combination of claim 6 wherein the cartridge includes a second elongated circumferential sidewall inwardly spaced from the first elongated circumferential sidewall, the first and second elongated circumferential sidewalls defining between them a first interior space.

12. The combination of claim 11 wherein the second elongated circumferential sidewall is disposable.

13. The combination of claim 11 wherein at least a part of the sleeve is disposed within the first interior space.

14. The combination of claim 13 wherein the cartridge has a first end and a selectively-moveable cover at the first end, the selectively-moveable cover moveable between an open position and a closed position, whereby a user may adjust access to the first interior space.

15. The combination of claim 14 wherein the selectively-moveable cover is disposable.

16. The combination of claim 11 wherein the second elongated circumferential sidewall is releasably connected to the first elongated circumferential sidewall.

17. The combination of claim 16 wherein the second elongated circumferential sidewall is connected directly to the first elongated circumferential sidewall.

18. The combination of claim 6 wherein the cartridge has a second end and a fastener at the second end, the fastener constructed and arranged to fasten the cartridge to the stethoscope.

19. The combination of claim 18 wherein the fastener includes a cap, the cap being releasably connected to the first elongated circumferential sidewall.

20. The combination of claim 19 wherein the cap includes an opening and a circumferential surface defining the opening, the circumferential surface constructed and arranged to secure the cap to the stethoscope.

21. The combination of claim 18 wherein the fastener is disposable.

22. The combination of claim 6 wherein the first elongated circumferential sidewall is disposable.

23. The combination of claim 1 wherein the cartridge is disposable.

24. A combination of a cartridge and a sleeve, the cartridge for mounting to a stethoscope, the sleeve for covering a head of a stethoscope, the combination comprising:

a cartridge having a first elongated circumferential sidewall, the first elongated circumferential sidewall defining an interior space; and a sleeve, at least a part of the sleeve being stored in the interior space, the cartridge and sleeve being constructed and arranged whereby the cartridge may be mounted to a stethoscope, and at least a part of the sleeve may be dispensed from the cartridge interior space and over a head of the stethoscope.

25. The combination of claim 24 wherein the cartridge has a first end and a selectively-moveable cover at the first end, the selectively-moveable cover moveable between an open position and a closed position, whereby a user may adjust access to the interior space.

26. The combination of claim 24 wherein the cartridge includes a second elongated circumferential sidewall inwardly spaced from the first elongated circumferential sidewall, the first and second elongated circumferential sidewalls defining between them a first interior space.

27. The combination of claim 26 wherein at least a part of the sleeve is disposed within the first interior space.

28. A cartridge for mounting to a stethoscope, and for dispensing a sleeve over a sensing head of a stethoscope, the cartridge comprising:

a first elongated circumferential sidewall;

a second elongated circumferential sidewall inwardly spaced from the first elongated circumferential sidewall, the first and second elongated circumferential sidewalls defining between them a first interior space, the first interior space constructed and arranged to contain at least a part of a sleeve;

a first end; and a selectively-moveable cover at the first end, the selectively-moveable cover moveable between an open position and a closed position, whereby a user may adjust access to the first interior space.

29. The cartridge of claim 28 wherein the selectively-moveable cover has an opening constructed and arranged to enable a head of a stethoscope to pass through the opening.

30. The cartridge of claim 28 further including a second end and a fastener at the second end, the fastener constructed and arranged to fasten the cartridge to a stethoscope.

31. The cartridge of claim 30 wherein the fastener includes a cap, the cap being releasably connected to the first elongated circumferential sidewall.

32. The cartridge of claim 31 wherein the cap includes an opening and a circumferential surface defining the opening, the circumferential surface constructed and arranged to secure the cap to a stethoscope.

* * * * *